United States Patent [19]

Nakayama et al.

[11] 4,289,916
[45] Sep. 15, 1981

[54] PROCESS FOR PRODUCING P-CHLOROALKYLBENZENE

[75] Inventors: Yoshiki Nakayama, Shimizu; Chihiro Yazawa, Yokohama; Koji Yamanashi, Shimizu, all of Japan

[73] Assignee: Ihara Chemical Industry Co., Ltd., Tokyo, Japan

[21] Appl. No.: 152,817

[22] Filed: May 23, 1980

[51] Int. Cl.³ .............................................. C07C 25/00
[52] U.S. Cl. .................................... 570/209; 570/210; 252/415
[58] Field of Search ................. 570/209, 208; 252/415

[56] References Cited

U.S. PATENT DOCUMENTS 4,069,264 1/1978 Lin ...................................... 570/209

Primary Examiner—Delbert E. Gantz
Assistant Examiner—Joseph A. Boska
Attorney, Agent, or Firm—Oblon, Fisher, Spivak, McClelland & Maier

[57] ABSTRACT p-Chloroalkylbenzene is selectively produced by chlorinating an alkylbenzene in the presence of a phenoxthine compound having the formula

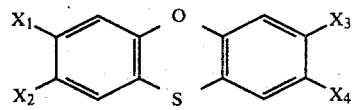

wherein $X_1$, $X_2$, $X_3$ and $X_4$ are the same or different and respectively represent hydrogen atom; an electron attractive group or an electron donative group and a Lewis acid or its precursor as a catalyst.

The process for producing a p-chloroalkylbenzene can be repeatedly carried out by separating the resulting a p-chloroalkylbenzene and adding a hydrogen halide to the residual mixture containing the catalyst to activate the catalyst and chlorinating a newly added alkylbenzene.

5 Claims, No Drawings

PROCESS FOR PRODUCING P-CHLOROALKYLBENZENE

BACKGROUND OF THE INVENTION

1. FIELD OF THE INVENTION

The present invention relates to a process for repeatedly producing p-chloroalkylbenzene in high selectivity.

2. DESCRIPTION OF THE PRIOR ARTS

The ring chlorinated alkylbenzenes are useful as reagents for various organic syntheses for producing medicines and agricultural chemicals etc. A demand of p-chloroalkylbenzenes such as p-chlorotoluene is large.

In the conventional chlorination of an alkylbenzene with chlorine gas in the presence of a Lewis acid such as antimony chloride, ferric chloride and aluminum chloride, an o-chloroalkylbenzene has been mainly produced and m-chloroalkylbenzene and polychlorinated compounds as by-products have been produced. It has been difficult to obtain a p-chloroalkylbenezene at a high yield such as higher than 40%.

In order to produce p-chloroalkylbenzene at high yield, various catalysts have been developed. For example, a p-chloroalkylbenzene has been produced at an yield of 45 to 52% by using a Lewis acid and sulfur or selenium as a catalyst. A p-chloroalkylbenzene has been produced at an yield of 55 to 60% by using a Lewis acid and thianthrene as the catalyst (Japanese Unexamined Patent Publication 19630/1977). The process using a Lewis acid and thianthrene as the catalyst give remarkably high selectivity to p-chloroalkylbenzene. However, thianthrene is oxidized in the presence of water to be converted through 5,5-dioxythianthrenes to diphenylsulfides. In the repeated use of the catalyst, the catalytic activity is lowered and the alkyl group as a side chain is chlorinated as a side-reaction.

The inventors have studied to develop a catalyst which give high selectivity to a p-chloroalkylbenzene but has not the disadvantages of thianthrene. As a result, the inventors have found that when a Lewis acid and a phenoxthine compound are used as the catalyst, the selectivity to the p-chloroalkylbenzene is high and the phenoxthine compound is only oxidized to 10-oxyphenoxthine in the presence of water and can be repeatedly used without a deterioration of the catalytic activity and a chlorination of the side chain as the alkyl group is not caused.

SUMMARY OF THE INVENTION

It is an object of the present invention to provide a process for producing a p-chloroalkylbenzene at high selectivity and high yield.

It is another object of the present invention is to provide a process for repeatedly producing a p-chloroalkylbenzene at high selectivity and high yield.

It is the other object of the present invention to provide a process for repeatedly using a catalyst in the production of a p-chloroalkylbenzene.

The foregoing and other objects of the present invention have been attained by chlorinating an alkylbenzene in the presence of a phenoxthine compound having the formula

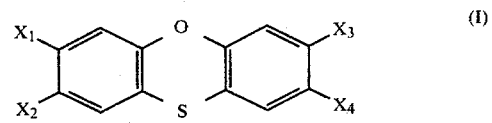

wherein $X_1$, $X_2$, $X_3$ and $X_4$ are the same or different and respectively represent hydrogen atom; an electron attractive group or an electron donative group and a Lewis acid or its precursor as a catalyst.

The process for producing a p-chloroalkylbenzene can be repeatedly carried out by separating the resulting a p-chloroalkylbenzene and adding a hydrogen halide to the residual mixture containing the catalyst to activate the catalyst and chlorinating a newly added alkylbenzene.

DETAILED DESCRIPTION OF THE PREFERRED EMBODIMENTS

The Lewis acids include not only Lewis acids themselves but also metals or metal compounds which form a Lewis acid during the chlorination or which impart a function of Lewis acid, for example, antimony, iron, tin, lead, aluminum, molybdenum and tellurium and halides, oxides, sulfides, carbonylates thereof.

Suitable Lewis acids include antimony trichloride, antimony pentachloride, aluminum chloride, antimony trifluoride, ferrous chloride, ferric chloride, antimony oxychloride, antimony trioxide, antimony tetraoxide, antimony pentaoxide, tellurium tetrachloride, ferric oxide, lead sulfide, ferrous sulfide, ferric sulfide, hexacarbonyl molybdenum, pentacarbonyl iron etc.

In the phenoxthine compounds having the formula (I), $X_1$, $X_2$, $X_3$ and $X_4$ respectively, represent hydrogen atom, an electron attractive group or an electron donative group and can be the same or different.

The electron attractive groups include halogen atoms such as chlorine, bromine and fluorine atoms; alkanoyl groups such as acetyl group; aroyl groups such as benzoyl group; nitro group, sulfonyl group, cyano group and trifluoromethyl group. The electron donative groups include alkyl groups and alkoxy groups. The phenoxthine compound can be used as a mixture. The phenoxthine compounds are preferably to have a degree of halogen substitution of 2 or more. Thus, even though the degree of halogen substitution is lower than 2, the ring chlorination of the phenoxthine compound is performed during the chlorination to have the degree of halogen substitution of higher than 2.0.

In the process of the present invention, a molar ratio of Lewis acid to the phenoxthine compound is in a range of 0.1 to 10:1 preferably 0.25 to 4:1.

In the ring chlorination of the alkylbenzene with such catalyst, the total amount of the Lewis acid and the phenoxthine compound is in a range of 0.001 to 5.0 wt. % preferably 0.01 to 1.0 wt. % based on the alkylbenzne. Chlorine gas is fed at the temperature of lower than the boiling point of the reaction mixture. When the temperature is too high, a production of the polychloride is increased thereby decreasing an yield of p-chloroalkylbenzene. On the other hand, the chlorination can be carried out at a low temperature of lower than minus several ten ° C. at high selectivity to p-chloroalkylbenzene, however, the reaction velocity is slow to be uneconomical. The reaction temperature is, therefore, in a range of 0° to 80° C. preferably 20° to 70° C. in the industrial operation.

The pressure of chlorine gas can be the atmospheric pressure, higher or lower pressure. In usual, the reaction is carried out under the atmospheric pressure.

The alkylbenzenes which are chlorinated with the catalyst can be mono-straight chain alkylbenzenes, mono-branched chain alkylbenzene, and preferably the alkylbenzene having a $C_1$-$C_4$ alkyl group.

When the catalyst of the present invention is used, the p-position of the alkylbenzene is effectively chlorinated to be lower chlorination at the o-position. The production of m-chloroalkylbenzene and polychlorinated alkylbenzene is remarkably small.

The catalyst has high stability and can be repeatedly used for the ring chlorination of the alkylbenzene for 5 to 6 times without adding or substituting the catalyst. However, the ring chlorination of the alkylbenzene are further repeated, the selectivity to the p-position is lowered. This is shown by the increase of the ratio of o-chloroalkylbenzene to p-chloroalkylbenzene (ratio of O/P).

The inventors have further studied to develop a process for preventing the lowering of the selectivity to the p-chloroalkylbenzene even in the repeat ring chlorinations of the alkylbenzene with the catalyst. As the result, it has been found that when the object products such as chloroalkylbenzenes are separated by a distillation etc. and then, the residue containing the catalyst is treated with a hydrogen halide, and the treated catalyst is repeatedly used for the ring-chlorination of the alkylbenzene, the ratio of O/P is not increased to obtain the p-chloroalkylbenzene at high yield.

The chlorinating agent can be thionyl chloride and hypochlorite preferably chlorine gas.

The recovery of the catalyst is carried out after separating the object products of the ring chloroalkylbenzenes by a distillation etc. Hydrogen halide is fed into the residue containing the catalyst at any desired stage.

Suitable hydrogen halides include hydrogen fluoride, hydrogen chloride and hydrogen bromide. The quantity and the time of the hydrogen halide are not critical and are preferably at a ratio of 20 to 1,000 ml/min. for 10 min. to 24 hours.

In the ring chlorination and the treatment for the activation of the catalyst, it is not always necessary to use a solvent. It is possible to use an inert solvent so as to smoothly perform the reaction. The alkylbenzene as the starting material can be used as a solvent. In the activation of the catalyst, the alkylbenzene can be remained in the residue.

In accordance with the process of the present invention, the hydrogen chloride as the by-product in the ring-chlorination of the alkylbenzene can be used. This is remarkably economical.

In accordance with this embodiment, p-chloroalkylbenzene can be repeatedly produced at high selectivity and the production of m-chloroalkylbenzene and polychloroalkylbenzene can be remarkably lowered. The catalyst can be repeatedly used so as to remarkably decrease the ratio of the catalyst to the p-chloroalkylbenzene. The quantity of the wasted solution and the residue can be decreased so as to be preferable from the viewpoint of the waste treatment. The industrial value of the present invention is remarkably high.

The present invention will be further illustrated by certain examples and references which are provided for purposes of illustration only and are not intended to be limiting the present invention.

EXAMPLE 1

In a 1 liter four necked flask equipped with a stirrer, a thermometer, a gas inlet and a refluxing condenser, 400 g. of cumene, 2 g. of antimony trichloride and 2 g. of phenoxthine were stirred and heated to about 50° C. on a water bath. After a constant temperature, chlorine gas was fed at a rate of 300 ml./min. The reaction temperature was maintained at 50° to 55° C. on the water bath. When chlorine gas was fed for 5 hours, the reaction was stopped. The reaction mixture was analyzed by a gas chromatography. A ratio of 2-chlorocumene to 4-chlorocumene (O/P) in the reaction mixture was 0.57.

EXAMPLE 2

In accordance with the process of Example 1 except using 424 g. of ethylbenzene instead of cumene, the reaction was carried out. As a result of the gas chromatography analysis, a ratio of 2-chloroethylbenzene to 4-chloroethylbenzene (ratio of O/P) in the reaction mixture was 0.68.

EXAMPLE 3

In accordance with the process of Example 1 except using toluene instead of cumene and varying a kind of the catalyst and an amount of the catalyst, the reaction was carried out. The ratios of 2-chlorotoluene to 4-chlorotoluene (ratio of O/P) in the reaction mixture were shown in Table 1.

TABLE 1

| | Catalyst | | | | |
|---|---|---|---|---|---|
| | Lewis acid | | Substituted phenoxthine | | |
| No. | Kind | Amount (g) | Kind | Amount (g) | Ratio of O/P |
| 1 | SbCl$_3$ | 2.00 | 2,3,7,8-TCPT | 2.00 | 0.89 |
| 2 | " | 0.10 | " | 0.14 | 0.85 |
| 3 | " | 0.01 | " | 0.03 | 0.78* |
| 4 | " | 0.10 | " | 0.20 | 0.86 |
| 5 | " | 1.00 | " | 0.30 | 0.81** |
| 6 | Sb | 0.10 | " | 0.28 | 0.85 |
| 7 | SbCl$_5$ | 0.24 | " | 0.28 | 0.86 |
| 8 | FeCl$_3$ | 0.15 | " | 0.70 | 0.90 |
| 9 | Fe | 0.35 | " | 0.70 | 0.91 |
| 10 | AlCl$_3$ | 0.55 | " | 0.70 | 0.92** |
| 11 | SnCl$_4$ | 0.45 | " | 0.70 | 0.86 |
| 12 | TeCl$_4$ | 0.55 | " | 0.70 | 0.99 |
| 13 | MoCl$_4$ | 0.55 | " | 0.70 | 0.98** |
| 14 | FeS | 0.20 | " | 0.70 | 0.93 |
| 15 | SbCl$_3$ | 0.10 | 2,8-DCPT | 0.14 | 0.85 |
| 16 | " | 0.10 | 2,3,8-TRCPT (15%) + 2,3,7,8-TCPT (85%) | 0.14 | 0.86 |
| 17 | " | 0.10 | 2,8-DCPT (3%) + 2,3,8-TRCPT (51%) + 2,3,7,8-TCPT (46%) | 0.14 | 0.86 |
| 18 | " | 0.10 | 2,8-DBPT | 0.40 | 0.87*** |
| 19 | SbCl$_3$ | 0.09 | 2,8-DM-3,7-DCPT | 0.20 | 0.85 |
| 20 | " | 0.09 | 2,8-DFPT | 0.60 | 0.86 |
| 21 | " | 0.09 | 2,3,7,8-TBPT | 0.20 | 0.87 |
| 22 | " | 0.09 | 2,8-DA-3,7-DCPT | 0.14 | 0.92** |
| 23 | SbOCl | 0.07 | 2,3,7,8-TCPT | 0.14 | 0.87 |

TABLE 1-continued

| | Catalyst | | | | |
|---|---|---|---|---|---|
| | Lewis acid | | Substituted phenoxthine | | Ratio |
| No. | Kind | Amount (g) | Kind | Amount (g) | of O/P |
| 24 | Sb$_2$O$_3$ | 0.06 | " | 0.14 | 0.87 |

Note:
PT: phenoxthine
2,3,7,8-TCPT: 2,3,7,8-tetrachlorophenoxthine
2,8-DCPT: 2,8-dichlorophenoxythine
2,3,8-TRCPT: 2,3,8-trichlorophenoxthine
2,8-dibromophenoxthine
2,8-DM-3,7-DCPT: 2,8-dimethyl-3,7-dichlorophenoxthine
2,8-DFPT: 2,8-difluorophenoxthine
2,3,7,8-TBPT: 2,3,7,8-tetrabromophenoxthine
2,8-DA-3,7-DCPT: 2,8-diacetyl-3,7-dichlorophenoxthine
2,8-DF-3,7-DCPT: 2,8-difluoro-3,7-dichlorophenoxthine
Reaction temperature:
*10 to 15° C.
**30 to 35° C.
***40 to 45° C.

EXAMPLE 4

In accordance with the process of Example 1 except using 0.10 g of SbCl$_3$ and 0.135 g. of 2,3,7,8-tetrachlorophenoxthine, the reaction was carried out so as to make clear the effect for repeating the catalyst. After the reaction, the ring chlorinated toluenes were separated by a distillation. Toluene was added to the residue and the catalyst was repeatedly used. The results are shown in Table 2.

As it is clear from Table 2, after the 6th times of the repeated used of the catalyst, the reaction was smoothly performed. A ratio of 2-chlorotoluene to 4-chlorotoluene (ratio of O/P) was 0.86–0.87. A side chain chlorinated toluene was not found. According to the gas chromatography analysis of 2,3,7,8-tetrachlorophenoxthine in the residue after the 6th times of the repeated uses of the catalyst, a mixture of 2,3,7,8-tetrachlorophenoxthine and 10-oxy-2,3,7,8-tetrachlorophenoxthine was found. In the mixture, 2,3,7,8-tetrachlorophenoxthine was at a ratio of 52%. The total of the mixture was corresponded to the original 2,3,7,8-tetrachlorophenoxthine.

TABLE 2

| | Catalyst | | | | |
|---|---|---|---|---|---|
| | Lewis acid | | Substituted phenoxthine | | Ratio |
| No. | Kind | Amount (g) | Kind | Amount (g) | of O/P |
| 1 | SbCl$_3$ | 0.09 | 2,3,7,8-tetrachloro-phenoxthine | 0.135 | 0.86 |
| 2 | | | first repeat | | 0.86 |
| 3 | | | second repeat | | 0.86 |
| 4 | | | third repeat | | 0.86 |
| 5 | | | fourth repeat | | 0.86 |
| 6 | | | fifth repeat | | 0.86 |
| 7 | | | sixth repeat | | 0.87 |

REFERENCE 1

In accordance with the process of Example 4 except using 0.142 g. of 2,3,7,8-tetrachlorothianthrene instead of 2,3,7,8-tetrachlorophenoxthine, the chlorination was carried out. The result is shown in Table 3.

TABLE 3

| | Catalyst | | | | |
|---|---|---|---|---|---|
| | Lewis acid | | Substituted thianthrene | | Ratio |
| No. | Kind | Amount (g) | Kind | Amount (g) | of O/P |
| 1 | SbCl$_3$ | 0.09 | 2,3,7,8-tetrachloro-thianthrene | 0.142 | 0.86 |
| 2 | | | first repeat | | 0.86 |
| 3 | | | second repeat | | 0.86 |
| 4 | | | third repeat | | 1.50 |

EXAMPLE 5

In a 1 liter four necked flask equipped with a stirrer, a thermometer, a gas inlet and a refluxing condenser, 368 g. of toluene, 0.1 g. of SbCl$_3$, 0.14 g. of 2,3,7,8-tetrachlorophenoxthine were charged and heated to 50° C. Chlorine gas was fed at a rate of 300 ml./min. under maintaining the temperature of 50° to 55° C. for 5 hours. After the reaction, the ring chlorinated toluenes were separated by a distillation. Toluene was added to the residue containing the catalyst and chlorine gas was fed again by the same manner to repeat the chlorination for 6 times. The ring chlorinated toluene was separated from the reaction mixture in the 6th reaction. The residue containing the catlyst was stirred and hydrogen chloride was fed at a rate of 100 ml./min. for 1 hour. Toluene was added and the chlorination was repeated for 7 times (total of 13 times).

The ratios of 2-chlorotoluene to 4-chlorotoluene (ratio of O/P) in each of the times, were in a range of 0.85 to 0.87 and any side chain chlorinated product was not found.

After the 6th time, the residue was analyzed to find the fact that 52% of 2,3,7,8-tetrachlorophenoxthine component was oxidized into 10-oxy-2,3,7,8-tetrachlorophenoxthine. After the treatment with hydrogen chloride, 80% of 2,3,7,8-tetrachlorophenoxthine component was remained. The total amount of 2,3,7,8-tetrachlorophenoxthine component was not varied from the first time to 13th times. No chemical change was found except that it was oxidized into 10-oxy-2,3,7,8-tetrachlorophenoxthine.

REFERENCE 2

In accordance with the process of Example 5 except that the residue containing the catalyst was not treated with hydrogen chloride before the 7th chlorination, the chlorination of toluene was repeated for 9 times. The ratios of 2-chlorotoluene to 4-chlorotoluene (ratio of O/P) were constant to be 0.86 from the beginning to the 6th time, and a side chain chlorinated toluene was not found. In the 7th time, the ratio of O/P=0.95; in the 8th time, the ratio of O/P=1.30; and in the 9th time, the ratio of O/P=1.5 and a large amount of the side branch chlorinated product was detected.

After the 9th time, only 10% of 2,3,7,8-tetrachlorophenoxthine was found and the residue was 10-oxy-2,3,7,8-tetrachlorophenoxthine.

EXAMPLE 6

In accordance with the process of Example 5 except varying the kind of the catalyst and the amount of the catalyst, each chlorination was carried out and the treatment with hydrogen chloride was carried out before the 7th reaction. The results are shown in Table 4.

TABLE 4

| No. | 1 | 2 | 3 | 4 | 5 | 6 | 7 | 8 |
|---|---|---|---|---|---|---|---|---|
| Alkylbenzene | Toluene | Toluene | Toluene | Toluene | Toluene | Toluene | Toluene | Toluene |
| Amount (g) | (368) | (368) | (368) | (368) | (368) | (368) | (368) | (368) |
| Lewis acid | $SbCl_3$ | $SbCl_3$ | $SbCl_3$ | $SbCl_3$ | $SbCl_3$ | Sb | $FeCl_3$ | Fe |
| Amount (g) | (0.10) | (0.10) | (0.10) | (0.10) | (0.12) | (0.05) | (0.07) | (0.02) |
| Catalyst | 2,8-DM-3,7-DCPT | 2,8-DBPT | 2,3,7,8-TCPT(85%) 2,3,8-TRCPT | 2,8-DCPT | 2,3,7,8-TCPT | 2,3,7,8-TCPT | 2,3,7,8-TCPT | 2,3,7,8-TCPT |
| Amount (g) | (0.13) | (0.17) | (0.14) | (0.11) | (0.14) | (0.14) | (0.14) | (0.14) |
| Reaction temp. (°C.) | 50–55° C. | 40–45° C. | 40–45° C. | 50–55° C. | 50–55° C. | 50–55° C. | 50–55° C. | 50–55° C. |
| Ratio of O/P Repeated times | | | | | | | | |
|  | 0.85 | 0.85 | 0.81 | 0.84 | 0.85 | 0.85 | 0.89 | 0.89 |
| 1 | 0.86 | 0.86 | 0.80 | 0.86 | 0.84 | 0.86 | 0.90 | 0.89 |
| 2 | 0.86 | 0.86 | 0.81 | 0.85 | 0.86 | 0.84 | 0.91 | 0.90 |
| 3 | 0.86 | 0.86 | 0.81 | 0.86 | 0.86 | 0.86 | 0.90 | 0.91 |
| 4 | 0.86 | 0.86 | 0.81 | 0.86 | 0.86 | 0.85 | 0.90 | 0.90 |
| 5 | 0.87 | 0.86 | 0.82 | 0.87 | 0.86 | 0.86 | 0.92 | 0.90 |
| 6 | 0.86 | 0.87 | 0.81 | 0.86 | 0.87 | 0.87 | 0.89 | 0.91 |
| 7 | 0.86 | 0.86 | 0.81 | 0.86 | 0.86 | 0.86 | 0.89 | 0.89 |
| 8 | 0.86 | 0.86 | 0.81 | 0.86 | 0.86 | 0.86 | 0.90 | 0.89 |
| 9 | 0.86 | 0.86 | 0.81 | 0.86 | 0.86 | 0.86 | 0.90 | 0.90 |
| 10 | 0.86 | 0.86 | 0.81 | 0.86 | 0.86 | 0.86 | 0.90 | 0.90 |
| 11 | 0.86 | 0.86 | 0.81 | 0.86 | 0.86 | 0.86 | 0.89 | 0.89 |
| 12 | 0.86 | 0.87 | 0.81 | 0.86 | 0.86 | 0.86 | 0.90 | 0.90 |
| 13 | 0.86 | 0.86 | 0.81 | 0.86 | 0.86 | 0.86 | 0.90 | 0.89 |

| No. | 9 | 10 | 11 | 12 | 13 | 14 | 15 |
|---|---|---|---|---|---|---|---|
| Alkylbenzene | Toluene | Toluene | Toluene | Toluene | Toluene | Toluene | Toluene |
| Amount (g) | (368) | (368) | (368) | (368) | (368) | (368) | (368) |
| Lewis acid | $SbCl_3$ | SbOCl | $Sb_2O_3$ | $SbCl_3$ | $SbCl_3$ | $SbCl_3$ | $AlCl_3$ |
| Amount (g) | (0.10) | (0.07) | (0.06) | (0.09) | (0.09) | (0.1) | (0.11) |
| Catalyst | 2,8-DCPT(3%) 2,3,8-TRCPT(51%) 2,3,7,8-TCPT(46%) | 2,3,7,8-TCPT | 2,3,7,8-TCPT | 2,3,7,8-TBPT | PT | 2,8-DA-3,7-DCPT | 2,3,7,8-TCPT |
| Amount (g) | (0.14) | (0.14) | (0.14) | (0.2) | (0.08) | (0.14) | (0.14) |
| Reaction temp. (°C.) | 50–55° C. | 50–55° C. | 50–55° C. | 40–45° C. | 50–55° C. | 30–35° C. | 30–35° C. |
| Ratio of O/P Repeated times | | | | | | | |
|  | 0.86 | 0.86 | 0.85 | 0.86 | 1.01 | 0.92 | 0.92 |
| 1 | 0.85 | 0.85 | 0.86 | 0.85 | 0.87 | 0.94 | 0.93 |
| 2 | 0.86 | 0.85 | 0.87 | 0.87 | 0.86 | 0.95 | 0.91 |
| 3 | 0.85 | 0.86 | 0.85 | 0.85 | 0.85 | 0.93 | 0.93 |
| 4 | 0.86 | 0.87 | 0.86 | 0.86 | 0.85 | 0.92 | 0.94 |
| 5 | 0.86 | 0.86 | 0.85 | 0.85 | 0.86 | 0.96 | 0.92 |
| 6 | 0.87 | 0.87 | 0.87 | 0.87 | 0.87 | 0.94 | 0.95 |
| 7 | 0.85 | 0.86 | 0.86 | 0.86 | 0.85 | 0.92 | 0.91 |
| 8 | 0.84 | 0.85 | 0.86 | 0.85 | 0.86 | 0.93 | 0.92 |
| 9 | 0.85 | 0.86 | 0.87 | 0.86 | 0.87 | 0.94 | 0.91 |
| 10 | 0.85 | 0.85 | 0.85 | 0.87 | 0.85 | 0.92 | 0.92 |
| 11 | 0.86 | 0.86 | 0.87 | 0.86 | 0.86 | 0.93 | 0.93 |
| 12 | 0.86 | 0.85 | 0.85 | 0.87 | 0.86 | 0.94 | 0.95 |
| 13 | 0.86 | 0.86 | 0.86 | 0.86 | 0.86 | 0.92 | 0.91 |

EXAMPLE 7

In accordance with the process of Example 5 except using 424 g. of ethylbenzene instead of 368 g. of toluene, the chlorination of ethylbenzene was repeated for 13 times. Before the 7th reaction, the treatment of the residue with hydrogen chloride set forth in Example 5 was carried out. The ratios of O/P of the resulting monochloroethylbenzenes were in a range of 0.60 to 0.64 and any side chain chlorinated compound was found.

EXAMPLE 8

In accordance with the process of Example 5 except using 480 g. of cumene instead of 368 g. of toluene, the chlorination of cumene was repeated for 13 times. Before the 7th reaction, the treatment of the residue with hydrogen chloride set forth in Example 5 was carried out. The ratios of O/P of the resulting monochlorocumenes were in a range of 0.45 to 0.48 and any side chain chlorinated compound was found.

EXAMPLE 9

In a 200 ml. four necked flask equipped with a stirrer, a thermometer, a gas inlet and a refluxing condenser, 1 mole of toluene, 0.01 mole of $SbCl_3$ and 0.01 mole of 2,3,7,8-tetrachlorophenoxthine were stirred and heated to about 50° C. Chlorine gas was fed at a rate of 100 ml./min. under maintaining the temperature of 50° to 55° C. for 4 hours. After the reaction, the ring chlorinated toluene was separated by a distillation. Toluene was added to the residue containing the catalyst and chlorine gas was fed again by the same manner to repeat the chlorination for 6 times. The ratios of O/P in each of the times were in a range of 0.85 to 0.87 and any side chain chlorinated product was not found.

After the 6th time, the residue was analyzed to find the fact that the catalyst remained as 48% of 2,3,7,8-tetrachlorophenoxthine and 52% of 10-oxy-2,3,7,8-tetrachlorophenoxthine.

When the ring chlorination of toluene was repeated for two times by using the catalyst, the ratio of O/P was increased to 1.3. After the 8th time, the residue was analyzed to find that the catalyst remained as 15% of 2,3,7,8-tetrachlorophenoxthine and 85% of 10-oxy-2,3,7,8-tetrachlorophenoxthine.

Into the residue, 106 ml. of toluene was added and hydrogen chloride was introduced at a rate of 100 ml./min. with stirring at a room temperature for 4 hours. The catalyst was recovered to 93% of 2,3,7,8-tetrachlorophenoxthine.

The ring chlorination of toluene was repeated by using the recovered catalyst. The ratio of O/P was 0.86. The result was the same as that of the newly added catalyst.

EXAMPLE 10

A residue obtained after repeating the chlorination of toluene to decrease the content of 2,3,7,8-tetrachlorophenoxthine in the catalyst to 5% was treated by the hydrogen chlorination of Example 9. As a result, the catalyst was recovered to have 89% of 2,3,7,8-tetrachlorophenoxthine.

The ring chlorination of toluene was carried out by using the recovered catalyst. The reaction was smoothly performed. A ratio of O/P was 0.87.

EXAMPLE 11

In accordance with the process of Example 9 except using the phenoxthine compounds shown in Table 5, the chlorination of toluene was repeated for 8 times. After the 8th time, the ratios of the remained phenoxthine compound in the residue to the original phenoxthine compound are shown in Table 5.

The residue was admixed with the solvent shown in Table 5 and hydrogen chloride was fed under the condition shown in Table 5.

The ratios of the phenoxthine compound after the recovery to the original phenoxthine compound are shown in Table 5.

TABLE 5

| No. | PT phenoxthine compound | PT in residue (%) | Recovery Solvent | Time (hr.) | Temp. (°C.) | Ratio of PT after recovery (%) |
|---|---|---|---|---|---|---|
| 1 | 2,3,7,8-TCPT | 5 | Toluene | 1.0 | 30 | 82 |
| 2 | " | 5 | " | 12.0 | 30 | 94 |
| 3 | " | 7 | " | 4.0 | 60 | 90 |
| 4 | " | 5 | Toluene 15% Dichlorotoluene 85% | 4.0 | 30 | 87 |
| 5 | " | 10 | Dichlorotoluene | 6.0 | 30 | 86 |
| 6 | " | 15 | o-Chlorotoluene | 2.0 | 30 | 87 |
| 7 | " | 15 | Toluene | 4.0 | 30 | 93 |
| 8 | 2,3,7,8-TBPT | 2 | " | 48.0 | 30 | 81 |
| 9 | " | 5 | " | 6.0 | 30 | 88 |
| 10 | 2,8-DM-3,7-DCPT | 12 | Cumene | 4.0 | 10 | 95 |
| 11 | 2,8-DB-3,7-DCPT | 15 | Ethylbenzene | 4.0 | 30 | 86 |
| 12 | 2,8-DF-3,7-DCPT | 13 | Toluene | 4.0 | 20 | 92 |
| 13 | 2,8-DA-3,7-DCPT | 15 | " | 4.0 | 30 | 93 |
| 14 | Cl—(phenoxthine)—Cl 1.9 / 2.0 | 15 | " | 4.0 | 30 | 94 |
| 15 | Cl—(phenoxthine)—Cl 1.85 / 2.0 | 30 | " | 4.0 | 40 | 88 |

The recovered catalysts were respectively used for the ring chlorination of toluene. Selectivities and activities are the same as those of the first time.

We claim:

1. A process for producing a p-chloroalkylbenzene which comprises chlorinating an alkylbenzene in the presence of a phenoxthine compound having the formula

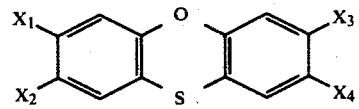

wherein $X_1$, $X_2$, $X_3$ and $X_4$ are the same or different and respectively represent hydrogen atom; an electron attractive group or an electron donative group and a Lewis acid or its precursor as a catalyst.

2. A process for producing a p-chloroalkylbenzene according to claim 1 wherein the resulting chloroalkylbenzenes are separated and a hydrogen halide is fed into the residue containing the catalyst to activate the catalyst and a newly added alkylbenzene is chlorinated.

3. A process for producing a p-chloroalkylbenzene according to claim 1 wherein Lewis acid or its precursor is selected from the group consisting of antimony trichloride, antimony pentachloride, aluminum chloride, antimony trifluoride, ferrous chloride, ferric chloride, antimony oxychloride, antimony trioxide, antimony tetraoxide, antimony pentaoxide, tellurium tetrachloride, ferric oxide, lead sulfide, ferrous sulfide, ferric sulfide, hexacarbonyl molybdenum and pentacarbonyl iron.

4. A process for producing a p-chloroalkylbenzene according to claim 1 wherein chlorine gas is fed into a mixture of an alkylbenzene and the catalyst.

5. A process for producing a p-chloroalkylbenzene according to claim 2 wherein a hydrogen halide is fed into a deactivated catalyst which is separated from the reaction product.

* * * * *

UNITED STATES PATENT AND TRADEMARK OFFICE
CERTIFICATE OF CORRECTION

PATENT NO. : 4,289,916
DATED : Sept. 15, 1981
INVENTOR(S) : YOSHIKI NAKAYAMA ET AL It is certified that error appears in the above-identified patent and that said Letters Patent are hereby corrected as shown below:

On The Title Page:

[30]--Foreign Application Priority Data

June 28, 1979 [JP]  Japan......81687

Jan. 24, 1980 [JP]  Japan......7319

Signed and Sealed this

Twenty-second Day of December 1981

[SEAL]

Attest:

GERALD J. MOSSINGHOFF

Attesting Officer    Commissioner of Patents and Trademarks